(12) United States Patent
Kirkegaard

(10) Patent No.: US 7,736,910 B2
(45) Date of Patent: Jun. 15, 2010

(54) ONE-STEP PRODUCTION OF GOLD SOLS

(75) Inventor: Leslie Kirkegaard, Ijamsville, MD (US)

(73) Assignee: Calypte Biomedical Corporation, Lake Oswego, OR (US)

( * ) Notice: Subject to any disclaimer, the term of this patent is extended or adjusted under 35 U.S.C. 154(b) by 1260 days.

(21) Appl. No.: 11/242,732

(22) Filed: Oct. 4, 2005

(65) Prior Publication Data

US 2007/0077187 A1 Apr. 5, 2007

(51) Int. Cl.
*G01N 33/553* (2006.01)
*G01N 33/53* (2006.01)
*B01J 13/00* (2006.01)
*C12Q 1/00* (2006.01)

(52) U.S. Cl. .................. 436/525; 436/805; 516/97; 530/391.5; 427/216; 435/6; 977/704; 977/722; 977/773; 977/810; 977/920; 977/924

(58) Field of Classification Search .............. 516/97; 436/525, 805; 530/391.5; 427/216; 435/975; 977/704, 722, 773, 810, 918, 920, 924
See application file for complete search history.

(56) References Cited

U.S. PATENT DOCUMENTS

| 4,313,734 | A | | 2/1982 | Leuvering |
| 4,761,181 | A | | 8/1988 | Suzuki |
| 5,294,369 | A | | 3/1994 | Shigekawa |
| 5,334,538 | A | | 8/1994 | Parker et al. |
| 5,384,265 | A | * | 1/1995 | Kidwell et al. .............. 436/525 |
| 5,556,756 | A | | 9/1996 | Olsen et al. |
| 5,616,467 | A | | 4/1997 | Olsen et al. |
| 5,637,508 | A | * | 6/1997 | Kidwell et al. .............. 436/525 |
| 6,103,538 | A | | 8/2000 | Kotsugai |
| 6,270,777 | B1 | | 8/2001 | Sokol et al. |
| 6,833,275 | B1 | | 12/2004 | Nichtl |
| 7,238,472 | B2 | * | 7/2007 | Mirkin et al. .................. 435/6 |

OTHER PUBLICATIONS

Hidenori Otsuka, Yukio Nagasaki, Kazunori Kataoka, "PEGylated nanoparticles for biological and pharmaceutical applications", Advanced Drug Delivery Reviews, Copyright © 2009 Elsevier B.V., pp. 403-419 (Feb. 2003).*
Geoghegan, W.D. and G.A. Ackerman, J. Histochem. Cytochem. 25: 1187-1200, Nov. 1977.
J.B. Calvert, Colloids at http://www.du.edu/~jcalvert/phys/colloid.htm (last modified Dec. 9, 2002).

* cited by examiner

*Primary Examiner*—Daniel S Metzmaier
(74) *Attorney, Agent, or Firm*—Pierce Atwood LLP; Kevin M. Farrell; David J. Wilson

(57) ABSTRACT

The present invention comprises novel "one-step" methods for the production of gold sol and gold sol conjugates. The methods disclosed herein produce gold sol and colloidal gold conjugates with product with yields on the order of about 20 ODs. Since current methods in the art yield conjugates at concentrations on the order of about 2 ODs, the present invention represents an approximately 10-fold increase in production over conventional methods. The novel method provided herein also does not result in the production of undesired aggregate by-products that, in conventional methods, must be removed via centrifugation, filtration or other means. The new method is therefore less labor intensive and requires less time to complete than standard methods in the art for synthesizing pure colloidal gold conjugates.

16 Claims, No Drawings

ONE-STEP PRODUCTION OF GOLD SOLS

FIELD OF THE INVENTION

This invention relates to the production of gold sol and the production of gold sol (colloidal gold) conjugates. The invention overcomes quality and efficiency problems in the prior art. The present invention provides a "one-step" method that does not result in the production of gold aggregates that must be removed from the sol by physical means. The "one-step" method of the present invention also produces gold sol at concentrations approximately 10-times those found in the prior art.

BACKGROUND

Colloidal gold solutions (gold sols) are useful in immunochemistry, bioresearch, and medical diagnosis and in the physical and chemical sciences. A gold sol is a suspension of gold particles measuring about 5 to 150 nm in either a flake or particle shape. The shape and size of the particle is important in permitting the particle to remain in suspension. In other words, the particles need a high surface-to-volume ratio. This geometry allows the particle to be subject to the forces of Brownian movement rather than the force of gravity thereby allowing it to remain in suspension.

Gold sols are used in research and medicine as, primarily, a labeling agent. Gold sol can be bound to proteinaceous molecules and other compounds facilitating their use as a labeling agent. Because of the electron dense nature of the gold particles, gold sol-conjugated labels are reagents of choice in electron microscopy, light microscopy, flow cytometry, blotting, hybridization assays and rapid diagnostic tests.

Current manufacturing methods for gold sol and gold sol-based conjugates are time consuming and labor intensive and/or have poor quality and quantity yields. The methods are dependent on precise chemical and physical parameters and often require "clean-up" steps involving ultracentrifugation, filtering or other mechanical means to remove gold sol aggregates (e.g., see, U.S. Pat. No. 6,833,275 B1 to Nichtl, which is herein incorporated by reference; Geoghegan, W. D. and G. A. Ackerman, J. Histochem. Cytochem. 25, 1187-1200, 1977). It is believed that aggregation occurs because current manufacturing procedures result in supersaturation of the gold particles in the solution. Because of the supersaturation, the gold sol particles form "nuclei." These nuclei facilitate aggregation in a process called nucleation. Controlling aggregation via optimized prior art manufacturing conditions is theoretically possible but in practice is hard to achieve (Chauduri, B. and S. Raychauduri, Manufacturing High-Quality Gold Sol, IVD Technology, March 2001). If not removed, the aggregates can cause the clumping of proteins (or other substances chosen to be gold sol-labeled) upon conjugation. These clumps then interfere with the protocol for which the gold sol conjugates are used.

Current manufacturing protocols also achieve relatively low yields. A concentration yielding an OD 530 nm reading of about 2 units is typical (see, e.g., U.S. Pat. No. 4,313,734 to Leuvering, which is herein incorporated by reference). Because of the labor intensity of the current manufacturing processes as well as the poor yields that are obtained, gold sol production is costly.

Additionally, gold sol conjugation is also not without problems. For example, conjugation of gold sol to thiol-containing molecules such as proteins often require the "coating" of the gold sol with n-alkanethiol and n-alkanethiol derivatives prior to conjugation (e.g., see, U.S. Pat. No. 5,294,369 to Shigekawa, which is herein incorporated by reference). These additional steps add even greater time and cost to an already expensive and labor-intensive undertaking.

What is needed are methods for the more efficient and economical production of gold sol and gold-sol thiol conjugates.

SUMMARY OF THE INVENTION

The present invention provides novel compositions and methods for the economical and efficient production of gold sol and gold sol conjugates without the aggregation problems of the prior art while also providing higher yields.

In general, one aspect of the invention provides a method for the production of gold sol where an activated reducing agent in solution in the presence of $CO_2$, $Au^{+++}$ and $Cl^-$ is used to form a suspension of gold sols. The solution is then contacted with a stabilizing agent sufficient to slow the reduction of $Au^{+++}$. Additionally, another aspect of the present invention provides a method of production of a gold sol conjugate wherein the suspension of gold sol produced by the procedure directly above is contacted with a thiol-containing agent in a buffered solution. The pH of the buffered solution is approximately 4-10. The reaction is ended with a blocking agent followed by a capping agent.

In one embodiment, the reducing agent used in the production of gold sol comprises ascorbic acid. In another embodiment, the reducing agent is activated by a primary amine. In yet another embodiment the primary amine is lysine. In still yet another embodiment the reducing agent is ascorbic acid provided at a molar ratio of ascorbic acid to lysine in the range of from about 150,000 to about 350,000. In still yet another embodiment, the molar ratio of ascorbic acid to lysine is about 250,000. In one aspect, the activated reducing agent is made by a reaction of relatively equal molar amounts of $HAuCl_4$, $KHCO_3$ and sodium ascorbate.

Many compounds can be used as a stabilizing agent in the invention. They may be selected from, for example, alkyl halides (e.g., chloroform, dichloromethane), alcohols (e.g., methanol, ethanol, isopropanol, butanol), ethers (e.g., dimethyl ether, ethyl methyl ether, diethyl ether, 1-ethoxypropane), glycols (e.g., 1,2-ethanediol, 1,2-propanediol 1,3-propanediol), ketones (e.g., acetone, ethyl metyl ketone 3-pentanone), esters (e.g., ethyl formate, methyl acetate, ethyl acetate) and amides (e.g., formamide, acetamide, succinamide) (see, e.g. U.S. Pat. No. 4,761,181 to Suzuki, which is incorporated herein by reference). In a preferred embodiment, the present invention contemplates that the stabilizing agent comprises isopropanol.

Any thiol-containing compound may be conjugated to the gold sol of the invention. In one aspect of the invention, the thiol-containing ligand comprises a protein. In another aspect, the thiol-containing ligand comprises Protein A. In yet another aspect, the thiol-containing ligand comprises an antibody. In yet another aspect, the thiol-containing ligand comprises an antigen, lectin, hormone receptor or enzyme receptor with a thiol-containing element.

The products of the thiol-conjugating reaction are also exposed to a blocking reagent. The blocking reagent is believed to reduce or prevent unwanted side reactions. In one embodiment the blocking agent comprises serum (e.g., goat, bovine, horse, chicken), gelatin, casein, albumin or synthetic substances, etc. In a preferred embodiment the blocking agent is bovine serum albumin (BSA).

As described in the detailed description, the thiol conjugation reaction is capped in order to end the reaction and stabilize the reaction products. In one embodiment, the capping is performed by, for example, methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH (see, e.g., U.S. Pat. No. 6,270,777 to Sokol, et al., which is incorporated herein by reference). In a preferred embodiment, the present invention contemplates that the capping agent comprises iodoacetic acid.

The gold sol producing reaction of the present invention requires a source of $CO_2$. In one aspect of the present invention the source of $CO_2$ comprises, for example, bicarbonate ($HCO_3$), sodium bicarbonate ($NaHCO_3$), ammonium bicarbonate ($NaH4CO_3$), potassium bicarbonate ($KHCO_3$), etc. In a preferred embodiment, the present invention contemplates that the source of $CO_2$ comprises $KHCO_3$.

The reactions of this invention take place in a buffered environment. In one embodiment, the reaction solution is buffered at a pH in the range of about 4 to 10. In another embodiment, the solution is buffered at a pH range of about 6.5 to 7.5. In yet another embodiment, the solution comprises any buffer that maintains the pH in the preferred range and does not react with the gold-conjugated ligand. In a preferred embodiment the buffer comprises HEPES buffered with NaOH.

The present invention requires a source of gold (Au). In one embodiment, the present invention contemplates that the source of $Au^{+++}$ and $Cl^-$ comprises $HAuCl_4$. In another embodiment, the source of $Au^{+++}$ is any gold salt (e.g., $AuCl_3$) or any gold halide (e.g., AuBr, AuI, etc.) that releases gold ions (e.g., $Au^{+++}$) upon contact with an aqueous solution.

DETAILED DESCRIPTION OF THE INVENTION

A. Gold Sol Production

The present invention is based on the finding that a novel method for synthesis of colloidal gold conjugates yields relatively pure product with yields on the order of about 20 ODs. Since current methods in the art yield conjugates at concentrations on the order of about 2 ODs, the present invention represents an approximately 10-fold increase in production over conventional methods. The novel method provided herein also does not result in the production of undesired aggregate by-products that, in conventional methods, must be removed via centrifugation, filtration or other means. The new method is therefore less labor intensive and requires less time to complete than standard methods in the art for synthesizing pure colloidal gold conjugates.

The invention relates to a method for conjugating a thiol-containing ligand to a gold particle. In short, this method comprises a) providing an activated reducing agent in solution in the presence of $CO_2$; b) contacting the solution of step a) with $Au^{+++}$ in the presence of $Cl^-$ to form a suspension of gold sols; c) contacting the suspension of step b) with a stabilizing agent sufficient to slow the reduction of $Au^{+++}$; d) contacting the suspension of step c) with a thiol-containing agent in a solution buffered at a pH in the range of about 4 to about 10, thereby conjugating the thiol-containing ligand to a gold particle; and e) contacting the gold particle conjugated to the thiol-containing ligand of step d) with a blocking agent and a capping agent, the blocking agent being characterized by the ability to terminate further conjugation of thiol-containing ligand to the gold particle, and the capping agent being characterized by the ability to cease reduction of the gold particle.

In this method, a gold particle conjugate is prepared by firstly forming red gold sols suitable for attachment to the thiol-containing ligand. To form red gold sols, an activated reducing agent is first provided in solution in the presence of $CO_2$. An activated reducing agent is made by treating a reducing agent with a composition comprising a primary amine effective to induce the creation of initiation sites on said agent. Suitable primary amines include, for example, Tris base, glycine, and lysine. In a preferred embodiment, the primary amine is lysine and the reducing agent is ascorbic acid. Preferably, an activated reducing agent is made by contacting lysine and ascorbic acid in solution at a molar ratio in the range of about 1:150,000 to about 1:350,000 lysine: ascorbic acid or, more preferably, in the range of about 1:200,000 to about 1:300,000 lysine: ascorbic acid, or most preferably at a ratio of about 1:250,000 lysine: ascorbic acid. When the primary amine comprises Tris base or glycine, for example, substantially higher concentrations of amine are desired. Optimum concentrations of Tris base, glycine, or other primary amine may be determined as described below.

In the formation of red gold sols, a preferred source of $CO_2$ is $HCO_3^-$ or $KHCO_3$. A preferred source of ascorbic acid is sodium ascorbate, a solution of which is prepared, preferably, within several hours or, most preferably, within two hours, of use in the present invention. Sodium ascorbate and $HCO_3^-$ are preferably used at a 1:1 ascorbate:$HCO_3^-$ molar ratio. Other $CO_2$ sources may be employed at concentrations that yield similar molar ratios of $CO_2$. When lysine is the primary amine, a solution of ascorbate-bicarbonate-lysine is incubated for at least 5-10 minutes or, preferably, about 10 minutes to activate the ascorbate. The timing of activation will vary and is dependent upon the identity and concentration of primary amine and reducing agent to be activated.

The term "reducing agent" is defined as a chemical agent with the ability to reduce $Au^{+++}$ to $Au^0$. An "activated reducing agent" is defined as a reducing agent with initiation or nucleation sites sufficient in number for preparing red gold sols. The number of initiation sites is an important factor in determining the optimal size of gold particles, sufficient stability of sols and the reproducibility of gold sol synthesis. Use of a stronger, more activated or more concentrated reducing agent (or use of longer incubation times with $Au^{+++}$) will result in the creation of more initiation sites for aggregation of gold atoms to occur. A high number of initiation sites will yield a high number of relatively small gold particles. Thus, if the reducing agent creates too many initiation sites and, therefore, is activated to a state beyond that which is sufficient to prepare red gold sols, contact of the reducing agent with $Au^{+++}$ will result in an undesirable black sol formation. Conversely, a low number of initiation sites will yield a low number of relatively large gold particles. Thus, if the reducing agent creates too few initiation sites and, therefore, is insufficiently activated to prepare red gold sols, contact of the reducing agent with $Au^{+++}$ will result in an undesirable yellow-brown sol formation. The degree of activation necessary is determined by the result to be achieved—namely, the production of red gold sols. Non-limiting examples are provided infra.

The solution of activated reducing agent with $CO_2$ is then contacted with $Au^{+++}$ in the presence of $Cl^-$ to form a suspension of red gold sols. Gold sol is formed from the reduction of $Au^{+++}$ to $Au^0$. Prior to contact of the activated reducing agent with $Au^{+++}$, all of the gold is in solution. Once contact occurs, the activated reducing agent induces reduction of gold ions to insoluble gold atoms, which aggregate at initiation sites. The presence of an initiation site such as provided by $CO_2$ during the reaction is critical to the formation of the desired red gold sols. In the absence of carbon dioxide (or other initiation site) the reaction yields an undesirable black or gold product. While not wishing to be bound by theory, it is likely that gold sols become red because they condense around micro-bubbles of, for example, $CO_2$ although others have speculated that the color of gold is a function of sol particle size. The desired red color of gold particles is a visual indicator of proper synthesis.

The presence of, for example, chloride ions in the synthesis of gold sols confers upon the gold particles a negative charge. While not wishing to be bound by theory, gold sols likely become soluble as they incorporate the provided negatively charged chloride ions into the sol. Also while not wishing to be bound by theory, the negative charge likely prevents unwanted aggregation of gold particles through electrostatic repulsion. As a result, chloride likely confers stability to the gold sols.

A preferred source of $Au^{+++}$ and $Cl^-$ is $HAuCl_4$. In one embodiment of the present invention, the reducing agent comprises activated sodium ascorbate, the source of $CO_2$ comprises $HCO_3^-$ and the source of $Au^{+++}$ and $Cl^-$ comprises $HAuCl_4$. Said reagents are preferably used for providing approximately equal ascorbate: $HCO_3^-$: $HAuCl_4$ molar ratios. In one embodiment, the molar ratios do not varying by more than about 10% for any one of the ascorbate, $KHCO_3$, and $HAuCl_4$. Next, the solution of sodium ascorbate, $KHCO_3$, and lysine is added to a solution of $HAuCl_4$ and, preferably, immediately mixed.

The resulting reaction is allowed to proceed for a minimal amount of time after which the suspension of gold sols is contacted for at least an hour with a stabilizing agent effective to slow the reduction of $Au^{+++}$. A preferred stabilizing agent for use in conjunction with the present invention comprises isopropyl alcohol. Although the present invention is not limited by theory, it is believed that the stabilizing agent works at least in part by dispersing the metal complexes uniformly in the solution. Slowing the reaction for at least an hour allows the practitioner to determine the optimum time to stop the reaction. The optimum time to stop the reaction is defined as the approximate time when gold sol production is maximized and aggregation is minimized.

After addition of the stabilizing agent, the reduction of $Au^{+++}$ is allowed to proceed until sufficient gold sol is formed. The amount of gold sol formed is preferably determined spectrophotometrically by assaying the absorption of the resulting suspension at 530 nm, the wavelength at which absorbance of red gold sols is maximized. As desired red gold sol production increases, the absorbance at 530 nm increases. As gold sol becomes over-reduced, however, the characteristic absorption maximum shifts to higher wavelengths, thereby decreasing O.D. readings at 530 nm. Thus, maximum gold sol production is characterized by readings of 18-20 O.D.'s at 530 nm.

B. Thiol Conjugation

After the production of gold sols, the suspension of gold sols is contacted with a thiol-containing agent in a solution buffered at a pH in the range of about 4 to about 10, thereby conjugating a thiol-containing ligand to a gold particle. A thiol-containing ligand or agent may be any ligand or agent containing free SH groups with the ability to be conjugated to gold sols. Thiol-containing agents include biomolecules such as proteins, glycoproteins, lectins, peptides, nucleic acids, and peptide nucleic acids. More specifically, thiol-containing agents include, for example, antibodies, antibody fragments, enzymes, antigens, hormones, streptavidin, avidin, biotin, Protein A, Protein G. or analogs thereof. The thiol-containing agent may be a synthetic, modified or naturally occurring compound. A thiol-containing agent is to be contacted with the gold sols under conditions where the agent is present in the conjugation reaction at a concentration sufficient to react with all or most of the available reaction sites on the gold sols but without excess ligand left unconsumed by the reaction. Once the reaction is complete, further contact of the gold sols with unconjugated ligand is undesirable since free thiol moieties over time will reduce gold sols to useless black precipitate. Optimum concentrations of thiol-containing agents are determined as the maximum concentration of thiol-containing agent that does not cause further reduction of gold, as determined by, for example, absorption at 530 nm.

Most ligand binding occurs best at relatively neutral pH conditions and, as such, the thiol-containing moiety is incubated with gold sol preferably in a solution buffered at a pH in the range of about 4 to about 10, more preferably in the range of about 6.5 to about 7.5 or, most preferably, at pH of about 7. A buffer substantially nonreactive with the conjugated gold is preferable for such purpose. Primary amines may facilitate oxidation of gold and, thus, use of a buffer that does not contain a primary amine is desirable. A preferred buffer comprises HEPES adjusted to about pH 7 with NaOH.

Timing of the conjugation reaction should be monitored for production of desired product. In a preferred embodiment, incubation of gold sol with thiol-containing ligand is to proceed for the minimum period of time for conjugation to occur. Incubations that proceed beyond this specified period cause the gold sol to form an undesirable precipitate. Reactions on the order of seconds are generally suitable for a ligand binding reaction to proceed to completion.

Once conjugation of the thiol-containing ligand to gold sol is complete, the conjugate is contacted with a blocking agent for stabilizing the synthesized product. The blocking agent is defined as an agent characterized by the ability to terminate further conjugation of thiol-containing ligand to the gold particle. The blocking agent serves to coat the gold particle and inhibit protein agglutination, which typically occurs under low salt conditions necessarily used in immunological and other binding assays. In the absence of blocking agent, gold sol conjugates could quickly precipitate out of solution, particularly upon contact with a test sample in a capture/detection assay. A preferred blocking agent comprises bovine serum albumin (BSA).

Following conjugation and blocking of the thiol-containing ligand to gold sol, the conjugate is contacted with a capping agent that additionally stabilizes the synthesized product. The capping agent is defined as an agent characterized by the ability to cease reduction of the gold particle. While not wishing to be bound by theory, the capping agent likely serves to suppress sulfur chemistry. A preferred capping agent comprises iodoacetic acid, which is well known in the art for capping thiol groups.

Because the present method does not require repeated centrifuge runs or other means to remove unwanted aggregates, the present invention may be regarded as a "one-step" method for synthesis of conjugated gold sols. In the absence of the required removal of unwanted aggregate necessary in prior art methods; synthesis of conjugated gold sols may be achieved in less time as compared to conventional methods, thereby greatly reducing labor and production costs. Also, reaction volumes in the present method are not limited to volumes that can be accommodated by centrifuge rotors. Thus, unlike conventional prior art methods, the present invention may be practiced on any scale, however small or large, where rapid mixing parameters can be managed. The present invention therefore provides significant production benefits over conventional prior art methods.

The yield of gold conjugates from the aforementioned reactions is dependent on the inertness of the reaction system. In a preferred embodiment, to maximize product yields, the method described herein is to be practiced using relatively pure reagents, sterile-filtered solutions and clean contact surfaces. For example, oily films on new plastic ware or trace contaminants from reagents and/or contact surfaces can greatly reduce stability of gold sols and lower product yields. Even seemingly harmless dirty and/or damaged stir bars can have significant detrimental effects on quality and yield of gold product.

The present invention is not intended to be limited by any particular use of a composition produced by the method provided herein. Many uses may be contemplated for the various embodiments of the present invention. For example, a composition produced by the method of the present invention may be utilized as a capture/detection reagent. In a preferred embodiment, a composition produced by the method of the present invention is useful as an immunological capture/detection reagent in an immunoassay for determination of an analyte in a sample. The composition may be employed in a competitive assay in which a gold-labeled analyte analogue or gold-labeled analyte-specific binder such as an antibody is used. The composition may further be employed in a sandwich assay in which a gold-labeled analyte-specific binder or a labeled additional binder with the ability to bind the analyte-specific binder is used. Suitable examples of such assays include pregnancy tests for the detection of human chorionic gonadotropin (HCG), or assays for the detection of analytes such as immunoglobulins such as anti-HIV antibodies. The composition may further be used in such assays as an aqueous suspension, or immobilized and/or lyophilized for example on a medium such as a chromatographic strip. The present invention is not intended to be limited by any particular use of a composition produced by the method provided herein. Additionally, the components of the present invention could be provided as a kit.

While specific embodiments of the present invention have been described, it will be apparent to those skilled in the art that various modifications thereto can be made without departing from the spirit and the scope of the invention as defined in the examples and appended claims. One of skill in the art will recognize that any of aforementioned specific reagents may be substituted for another or other reagents with similar or identical properties, based on the principles outlined above. One of skill in the art may substitute specifically named reagents for any of the specific purposes specified above; i.e., to provide an alternate source of $CO_2$, $Au^{+++}$ or $Cl^-$; to activate or act as a reducing agent; to buffer the conjugation of a thiol-containing ligand to the gold particle; to coat the gold particle and inhibit protein agglutination; and/or to cease reduction of the gold particle. Using a preferred embodiment as described herein, one of skill in the art may substitute a reagent, or multiple reagents one at a time, to test and/or optimize conditions for use of that reagent or reagents. A series of reactions may be carried out in parallel with the substituted reagent to be tested, with reactions varying incubation times and concentrations of the substituted reagent, until the desired result is achieved -namely, synthesis of relatively pure gold conjugates at high yields.

EXPERIMENTAL

The following examples serve to illustrate certain preferred embodiments and aspects of the present invention and are not to be construed as limiting the scope thereof.

Example 1

This example represents a method for the production of gold sol and gold sol conjugated thiol-containing compounds.

Gold sol is formed from the reduction of strongly acetic $HAuCl_4$. Distilled water (4.943 ml) was mixed with 0.055 ml 1 M Na-ascorbate, 0.055 ml 1 M $KHCO_3$ and 0.022 ml lysine at a concentration of mg/ml. The reaction was allowed to proceed for approximately 10 min at room temperature (RT). Next, the mix above was added to 4.934 ml of 0.4% $HAuCl_4$ and mixed rapidly for 1 min. Next, 0.10 ml of 70% isopropyl alcohol was added to slow the rate of the reaction. OD was monitored as A530 and the reaction was stopped when absorbency reached between about 18-20 OD.

Gold sol conjugated thiol-containing agents (in this example, protein A) were made by adding the gold sol solution above to a buffered solution of protein A (0.005 ml at 10 mg/ml, stock solution protein A added to 0.25 ml HEPES-NaOH, pH 7.0). The reaction was allowed to proceed for 10 sec and was stopped by adding a blocking agent (0.1 ml of 10% bovine serum albumin, BSA) to the reaction. The reaction was then capped with 0.2 ml of iodoacetic acid at 10 mg/ml. Absorbance was measured at 530 nm.

Example 2

This example represents a second method for the production of gold sol and gold sol conjugated thiol-containing compounds.

Gold sol solution was formed by first heating 600 ml of distilled water to a boil. 12.5 ml was removed and 0.21 g of sodium citrate tribasic dihydrate was added with mixing until dissolved. Next, 3.0 ml of refrigerated 4% gold stock solution was added to the 600 ml boiling water. Next, the sodium citrate solution made above was added to the 600 ml of gold/water mixture. When the solution darkened to a purple color it was boiled for another 10 min. At the end of the 10 min the solution was cooled on the bench top. Alternatively, ice may be used to accelerate the cooling process.

Protein A conjugate was formed by first, stirring 600 ml of the gold solution from above and stirring. Next, 3.0 ml of 1 M HEPES 7.0 was added to the gold solution. Next, 360 µl of protein A (at about 10 mg/ml) was added. The solution was then mixed on a spin plate for 30 min. Next, 60 ml of 1% BSA solution was added and let spin (on a spin plate) for 5 min. The vessel was removed and the solution placed in centrifuge tubes and centrifuged at 5500 rpm for 50 min to concentrate the protein A-gold sol conjugate. After centrifugation, the supernatant was aspirated off and the pellets were resuspended by vortexing in the residual solution in the centrifuge tubes and then combined. Each tube was rinsed with approximately 1.0 ml of resuspension buffer (1% BSA, 0.25 M Mops pH 8.0, 0.5% PEG8000, 1:1000 of Proclin (enzyme save antibiotic)) and added to the combined pellets. Next, the OD reading was taken at 530 nm after dilution of 1:100 in 1.0 ml resuspension buffer.

As is evident from the forgoing, other methods of practicing the invention disclosed herein will be apparent to those practiced in the art and such embodiments of the present invention are included within the scope of this invention. As will also be evident from the forgoing, the present invention provides methods for the production of gold sol and gold sol conjugates that are a substantial improvement both in efficiency and economy over prior art methods.

I claim:

1. A method for producing a gold sol, the method comprising:
   a) providing an activated reducing agent in solution in the presence of $CO_2$, wherein the reducing agent comprises ascorbic acid or sodium ascorbate and is activated with a primary amine;
   b) contacting the solution of step a) with $Au^{+++}$ in the presence of $Cl^-$ to form a suspension of red color gold sols;
   c) contacting the suspension of step b) with a stabilizing agent sufficient to slow the reduction of $Au^{+++}$.

2. A method for conjugating a thiol-containing ligand to a gold particle, the method comprising:
   a) providing an activated reducing agent in solution in the presence of $CO_2$, wherein the reducing agent comprises ascorbic acid or sodium ascorbate and is activated with a primary amine;
   b) contacting the solution of step a) with $Au^{+++}$ in the presence of $Cl^-$ to form a suspension of red color gold sols;
   c) contacting the suspension of step b) with a stabilizing agent sufficient to slow the reduction of $Au^{+++}$;
   d) contacting the suspension of step c) with a thiol-containing agent in a solution buffered at a pH in the range of about 4 to about 10, thereby conjugating the thiol-containing ligand to a gold particle; and
   e) contacting the gold particle conjugated to the thiol-containing ligand of step d) with a blocking agent and a capping agent, the blocking agent being characterized by the ability to terminate further conjugation of thiol-containing ligand to the gold particle, and the capping agent being characterized by the ability to cease reduction of the gold particle.

3. The method of claim 2 wherein the primary amine is lysine.

4. The method of claim 3 wherein the reducing agent is ascorbic acid provided at a molar ratio of ascorbic acid to lysine in the range of from about 150,000 to about 350,000.

5. The method of claim 4 wherein the molar ratio of ascorbic acid to lysine is about 250,000.

6. The method of claim 2 wherein the activated reducing agent is made by a reaction of relatively equal molar amounts of $KHCO_3$ and Sodium Ascorbate.

7. The method of claim 2 wherein the stabilizing agent comprises isopropanol.

8. The method of claim 2 wherein the thiol-containing ligand comprises Protein A.

9. The method of claim 2 wherein the thiol-containing ligand comprises an antibody.

10. The method of claim 2 wherein the capping agent comprises iodoacetic acid.

11. The method of claim 2 wherein the blocking agent comprises BSA.

12. The method of claim 2 wherein the source of $CO_2$ comprises $KHCO_3$.

13. The method of claim 2 wherein the solution is buffered at a pH in the range of about 6.5 to 7.5.

14. The method of claim 13 wherein the solution comprises HEPES buffered with NaOH.

15. The method of claim 2 wherein the source of $A^{+++}$ and $Cl^-$ comprises $HAuCl_4$.

16. The method of claim 2, wherein said method does not require removal of unwanted aggregates.

* * * * *